United States Patent [19]

Gray

[11] 4,423,729

[45] Jan. 3, 1984

[54] SUTURE INSTALLATION INSTRUMENT

[76] Inventor: Robert C. Gray, 280 Clifford, Blackfoot, Id. 83221

[21] Appl. No.: 307,841

[22] Filed: Oct. 2, 1981

[51] Int. Cl.$^3$ .................. A61B 17/04; A61B 17/32; B26B 13/00
[52] U.S. Cl. ............................. 128/334 R; 128/318; 30/233
[58] Field of Search ........... 128/326, 318, 321, 334 R; 30/131, 134, 154, 233, 271, 200

[56] References Cited

U.S. PATENT DOCUMENTS

| 619,326 | 2/1899 | Merrill | 30/233 |
| 4,271,838 | 6/1981 | Lasner et al. | 128/318 |

FOREIGN PATENT DOCUMENTS 192902 12/1907 Fed. Rep. of Germany ........ 30/233

Primary Examiner—Henry J. Recla
Assistant Examiner—Karin M. Reichle
Attorney, Agent, or Firm—Richard F. Bojanowski

[57] ABSTRACT

The blades of a pair of suture scissors are pivotably mounted within a tapered hood. The nose of the hood is smoothly curved and a slot is formed thereacross such that the plane of the slot is in parallel alignment with the shearing line of the blades of the scissors. The width of the slot is such as to accommodate suture threads but not great enough to receive a knot in the suture. The mouth of the slot is smoothly curved to provide convex surfaces to assist in guiding the suture threads into the slot.

3 Claims, 3 Drawing Figures

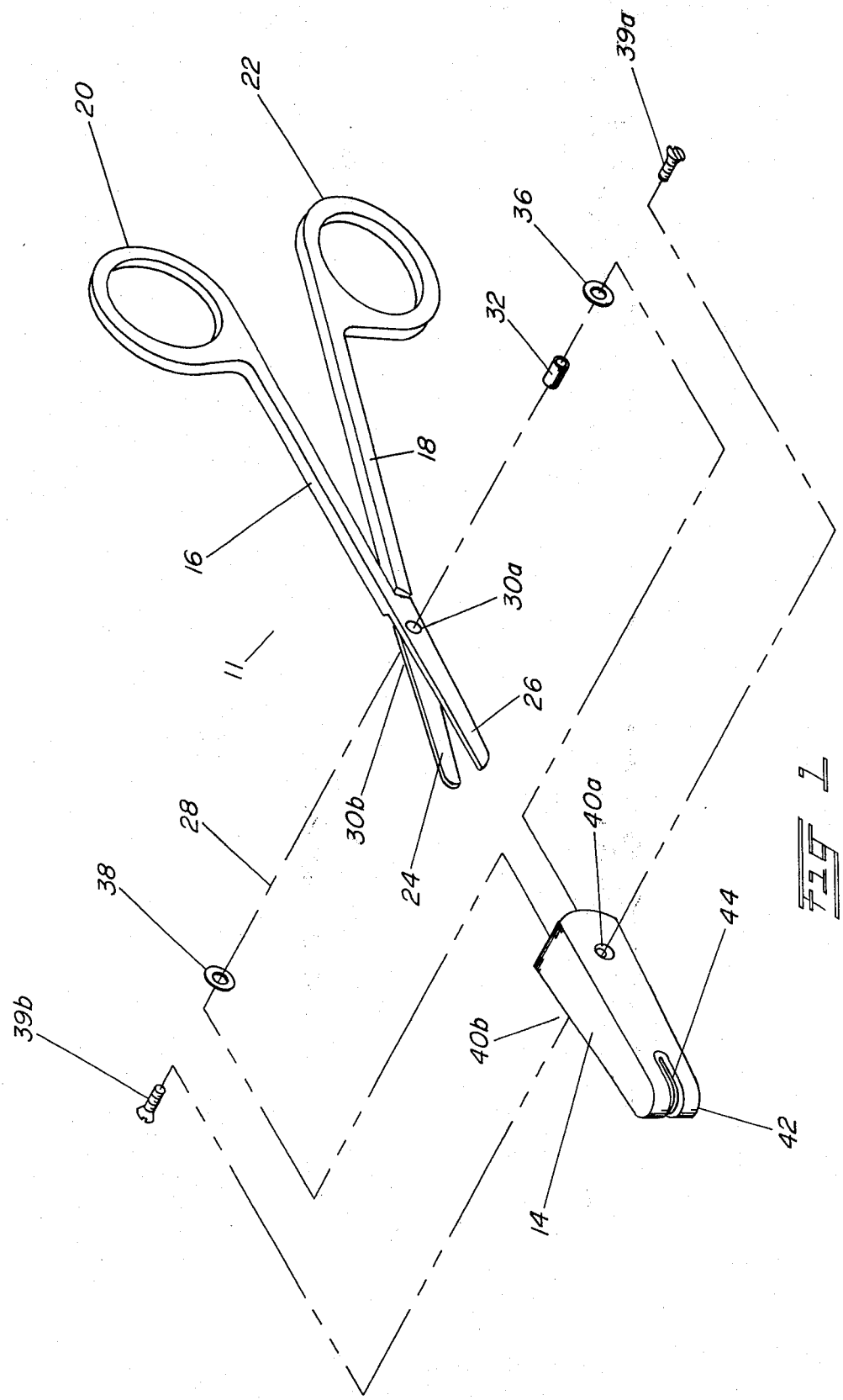

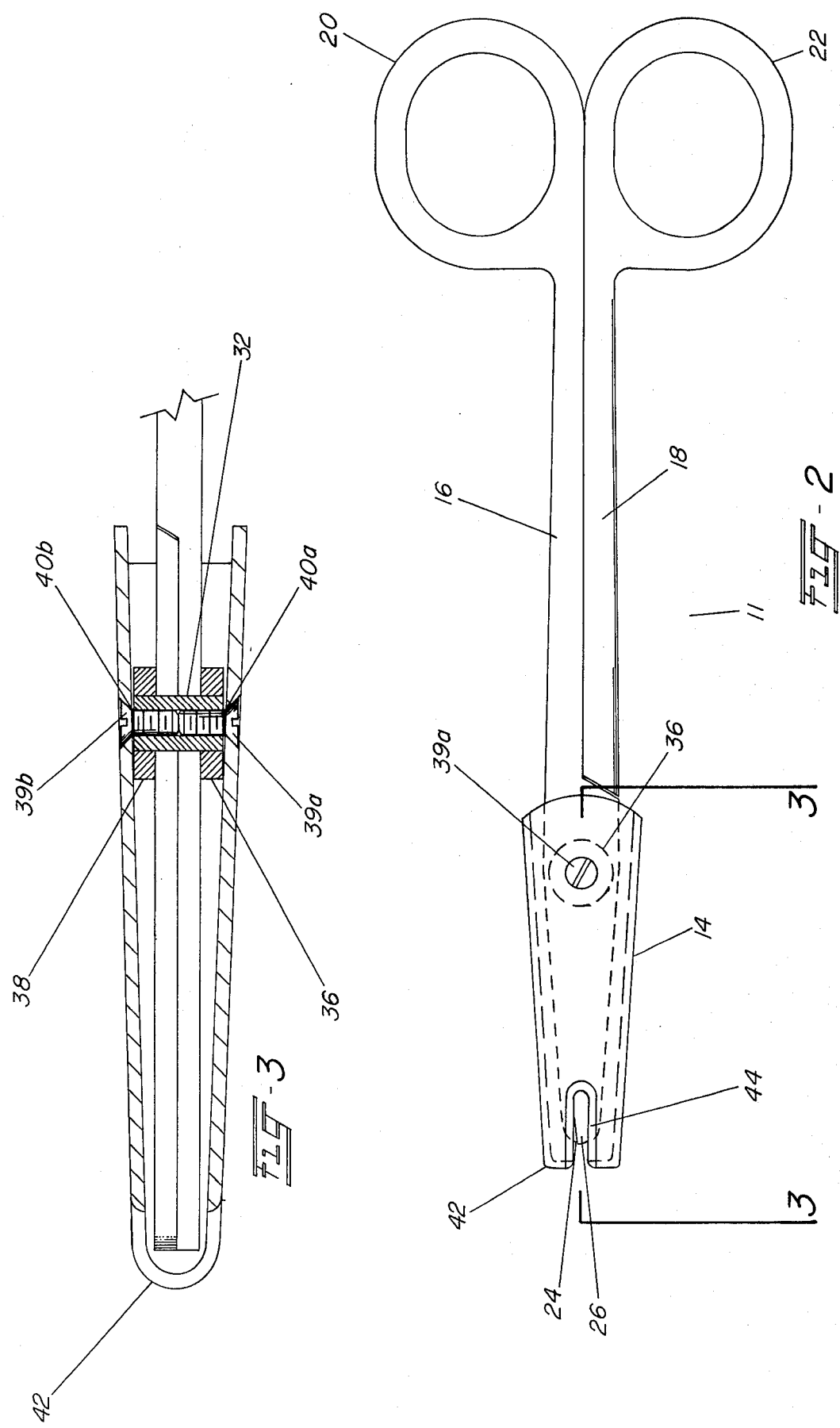

SUTURE INSTALLATION INSTRUMENT

FIELD OF THE INVENTION

The present invention relates to medical instruments and, more particularly, to an improved device for use in installing sutures.

BACKGROUND OF THE INVENTION

Suturing, the stitching together of human flesh which has been cut or otherwise separated, requires careful avoidance of further injury or trauma to the tissue being sutured or adjacent tissue. At the same time, however, suturing must be done quickly and effectively. For example, once a suture has been inserted and tied, its free ends must be severed without jeopardizing the integrity of the suture or causing trauma to the surrounding tissue.

In the prior art, various scissor-like instruments are known for use in removing sutures quickly and without injury to healed flesh. The present invention, by way of contrast, is particularly adapted for use in the installation of sutures. More particularly, the present instrument is utilized to sever the suture threads in an expeditious manner while safeguarding the sutures as well as the surrounding tissue. It is particularly adapted to preserve a suture, whereas conventional devices are best adapted to remove and, thereby, to destroy sutures.

DRAWINGS

Further objects and advantages of the present invention can be readily ascertained from the following description and appended drawings. In the drawings, which are offered by way of example but not in limitation to the present invention:

FIG. 1 is a pictorial exploded view of the present invention partially disassembled;

FIG. 2 is a side profile of the instrument of FIG. 1 in an assembled condition with portions cut away for purposes of clarity; and FIG. 3 is a sectional view taken along the line 3—3 in FIG. 2 for viewing in the direction of the arrows.

DETAILED DESCRIPTION OF THE PREFERRED EMBODIMENT

Referring now to FIG. 1, the instrument of the present invention generally includes a pair of suture scissors 11 in cooperative relationship with a tapered hood member 14. As will be discussed in detail hereafter, the hood member 14 serves the functions of guiding and measuring the suture thread while safeguarding the suture knot and surrounding tissue.

The scissors 11 comprise a pair of crossed members 16 and 18 having finger openings 20 and 22 at the non-cutting end. The working end of the scissors includes blades 24 and 26 in a conventional side-by-side shearing engagement. The blades are pivoted about an axis 28, defined by registered apertures 30a and 30b, whose centerline extends perpendicular to the shearing line of the blades 24 and 26. In the preferred embodiment, a tubular pivot shaft 32 is mounted to extend through the registered apertures to define an axle for rotation of the blades 24 and 26. Washers 36 and 38 are mounted at opposite ends of the shaft 32 to act as bearing surfaces and to provide alignment for the hood member 14. Preferably, washers 36 and 38 are riveted to the shaft 32 and thereby provide the necessary tension to the shearing blades for facilitating cutting.

Hood member 14, best illustrated in FIGS. 2 and 3, generally comprises a tapered sheath having a hollow interior which is dimensioned to receive blades 24 and 26 and to accommodate limited pivoting thereof. The width of the interior of the hood only slightly exceeds the width of the side-by-side blades. The other transverse dimension or breadth of the interior of the hood (designated as Dimension "a" in FIGS. 1 and 2) is such as to permit pivotal manipulation of the blades. The hood member 14 is secured to the blades by the pivot shaft 32 which extends transversely across the interior of the hood through opposed holes 40a and 40b proximal the larger end of the hood. If the washers are not riveted to the shaft, the entire assembly is secured by screws 39a and 39b which thread into the ends of the tubular pivot shaft 32. With this arrangement, the washers 36 and 38 are held against the sides of the hood member 14 and hold scissors 11 within hood 14. The larger end of the hood member 14 is fully open to accommodate pivotal working of the scissors.

The smaller end 42, or nose, of the tapered hood 14 is smoothly convex across its width. A slot 44 is formed across the nose with the plane of the slot in parallel alignment with the shearing line of the blades 24 and 26. The width of the slot 44 is such as to accommodate suture threads but not great enough to receive a knot in the suture. In practice, the optimal depth of the slot 44 has been found to be about 5/32 inch. (A convenient length for the hood member has been found to be about 1⅜ inch; a turn, this determines the maximum length of the blades 24 and 26). Preferably, the mouth of the slot 44 is smoothly curved to provide convex surfaces to assist in guiding the suture threads into the slot.

The depth of the slot 44 is related to the aforementioned dimension "a" at the nose of the hood. More specifically, the interior breadth of the hood must be adequate to permit the blades to open sufficiently to freely accept the suture threads at the back of the slot. By way of contrast, if the blades cannot part completely at the back of the slot, suture threads could be severed unintentionally.

The use and operation of the suture installation instrument of the present invention can now be understood. When a suture is stitched and tied, the suture threads must be severed before the next suture can be installed. To sever the threads, the described instrument is manipulated into a position such that both threads are accepted into the slot 44 in the nose of the hood. This is readily accomplished because the threads are guided by the curved mouth of the slot. In turn, the threads serve as a guide in positioning the instrument against the knot of the suture. (This feature has been found to be particularly convenient in suturing in fatty tissue.) During such manipulation, the blades 24 and 26 of the scissors are pressed apart to abut against the interior of the hood member 14; this makes the instrument rigid and easily maneuverable. (When using conventional scissors, by way of contrast, the blades are exposed and must be carefully positioned or else surrounding flesh and organs will be cut or pierced.) Once the threads of the suture are within the slot 44, the blades of the scissors can be worked easily to sever the threads.

As mentioned previously, the slot 44 is too narrow to accept the knot in the suture. Accordingly, the hood 14 further serves to space the suture knot from the shearing line of the blades 24 and 26. As a result, the threads of the suture are cut at a predetermined distance (about ⅛ inch) from the knot, thereby maintaining the integrity of the knot.

I claim:

1. An instrument for use in installing sutures comprising:
   (a) a pair of scissors having blades defining a shearing line;
   (b) a tapered hood member having a rounded nose portion and a hollow interior dimensioned to receive said blades and to permit pivotal manipulation thereof;
   (c) pivot means extending transversely across the interior of said hood member for positioning said hood member in relation to said blades and to provide an axle for pivotal rotation of said blades within said hood and wherein said pivotal means includes a tubular shaft extending through said hood member and said blades to secure said shaft in position;
   (d) slot means formed across said nose of said hood member, the plane of said slot means being in parallel alignment with the shearing line of said blades, the width of said slot means being related to the breadth of the interior of the hood member such that the blades can be parted sufficiently to permit suture threads to be accommodated at the back of said slot.

2. An instrument according to claim 1 wherein the depth of said slot is about 5/32 inch.

3. An instrument according to claim 1 wherein the mouth of said slot is smoothly curved to provide convex surfaces to guide suture threads into said slot means.

* * * * *